United States Patent
Xie et al.

(10) Patent No.: US 10,781,431 B2
(45) Date of Patent: Sep. 22, 2020

(54) CARDIOTONIC STEROID ANTAGONISTS AND RELATED METHODS

(71) Applicant: MARSHALL UNIVERSITY RESEARCH CORPORTION, Huntington, WV (US)

(72) Inventors: Zijian Xie, Huntington, WV (US); Moumita Banerjee, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 15/129,534

(22) PCT Filed: Apr. 2, 2015

(86) PCT No.: PCT/US2015/024124
§ 371 (c)(1),
(2) Date: Sep. 27, 2016

(87) PCT Pub. No.: WO2015/160529
PCT Pub. Date: Oct. 22, 2015

(65) Prior Publication Data
US 2017/0183639 A1    Jun. 29, 2017

Related U.S. Application Data

(60) Provisional application No. 61/974,252, filed on Apr. 2, 2014.

(51) Int. Cl.
*A61K 38/00* (2006.01)
*C12N 9/14* (2006.01)
*C12Q 1/50* (2006.01)
*C12Q 1/48* (2006.01)
*G01N 33/573* (2006.01)
*G01N 33/50* (2006.01)
*C07K 7/08* (2006.01)
*A61K 38/46* (2006.01)
*A61K 45/06* (2006.01)

(52) U.S. Cl.
CPC ............ *C12N 9/14* (2013.01); *A61K 38/46* (2013.01); *A61K 45/06* (2013.01); *C07K 7/08* (2013.01); *C12Q 1/485* (2013.01); *C12Q 1/50* (2013.01); *C12Y 306/03009* (2013.01); *G01N 33/5044* (2013.01); *G01N 33/573* (2013.01); *A61K 38/00* (2013.01); *C07K 2319/00* (2013.01); *C07K 2319/01* (2013.01); *G01N 2333/3153* (2013.01); *G01N 2333/3156* (2013.01); *G01N 2333/91* (2013.01); *G01N 2333/9723* (2013.01)

(58) Field of Classification Search
CPC .................................. A61K 38/46; C12N 9/14
See application file for complete search history.

(56) References Cited

U.S. PATENT DOCUMENTS

| | | | | |
|---|---|---|---|---|
| 2011/0020437 A1* | 1/2011 | Otterlei | ............. | C07K 14/4738 424/450 |
| 2011/0172164 A1* | 7/2011 | Pellecchia | ............ | C07D 213/56 514/20.8 |
| 2013/0150294 A1 | 6/2013 | Xie et al. | | |

FOREIGN PATENT DOCUMENTS

| | | | | |
|---|---|---|---|---|
| CA | 2667251 A1 * | 5/2008 | ............. | A61K 38/45 |
| CA | 2667251 A1 * | 5/2008 | ............. | A61K 38/45 |
| WO | 2011/088210 A1 | 7/2011 | | |
| WO | WO-2011088210 A1 * | 7/2011 | ............... | C12Q 1/34 |
| WO | 2015/160529 A1 | 10/2015 | | |

OTHER PUBLICATIONS

Senis, Src family kinases: at the forefront of platelet activation, Blood. Sep. 25, 2014;124(13):2013-24.*
Soltoff (Regulation and Identification of Na,K-ATPase alpha-1 Subunit Phosphorylation in Rat Parotid Acinar Cells, JBC 2010, vol. 285, No. 47) (Year: 2010).*
U.S. Patent and Trademark Office, International Search Report issued in corresponding Application No. PCT/US2015/024124, dated Jul. 20, 2015.
International Bureau of WIPO, International Report on Patentability issued in corresponding Application No. PCT/US2015/024124, dated Oct. 4, 2016.
European Patent Office, Supplementary European Search Report issued in corresponding Application No. EP15779886, dated Aug. 4, 2017.
Moumita Banerjee, "A Model for Domain Specific Regulation of Src Kinase by alpha-1 subunit of Na/K ATPase.".
Bernard A. Liu, et al. "The language of SH2 domain interactions defines phosphotyrosine-mediated signal transduction," FEBS Letters, vol. 586, No. 17, 2012, p. 2597-2605.
China National Intellectual Property Administration, First Office Action issued in corresponding Application No. 201580023851.0, dated May 7, 2019.

* cited by examiner

Primary Examiner — Jeanette M Lieb
(74) Attorney, Agent, or Firm — Stites & Harbison, PLLC; Terry L. Wright

(57) ABSTRACT

Non-naturally occurring peptides are provided that act as a Src SH2 domain antagonist of cardiotonic steroids. Pharmaceutical compositions comprising the peptides are also provided along with vectors encoding the peptides. Methods of treating a Src-associated disease and reducing Src activity in a cell are further provided and include administering or contacting a cell with an effective amount of the peptide.

18 Claims, 9 Drawing Sheets

Specification includes a Sequence Listing.

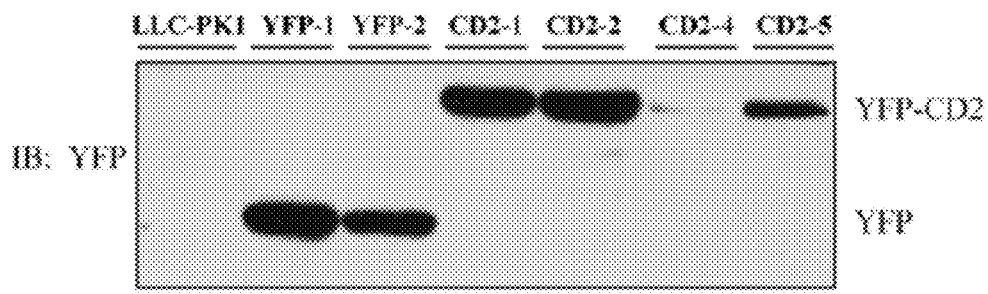
FIG. 3C
KSSKIMESFK NMVPQQALVI RNGEKMSINA EEVVVGDLVE VKGGDRIPAD LRIISANGCK VDNSSLTGES
EPQTRSPDFT NENPLETRNI AFFSTNCVEG TARGIVVYTG DRTVMGRIAT LASGLEGGQT PIAAEI
FIG. 4A
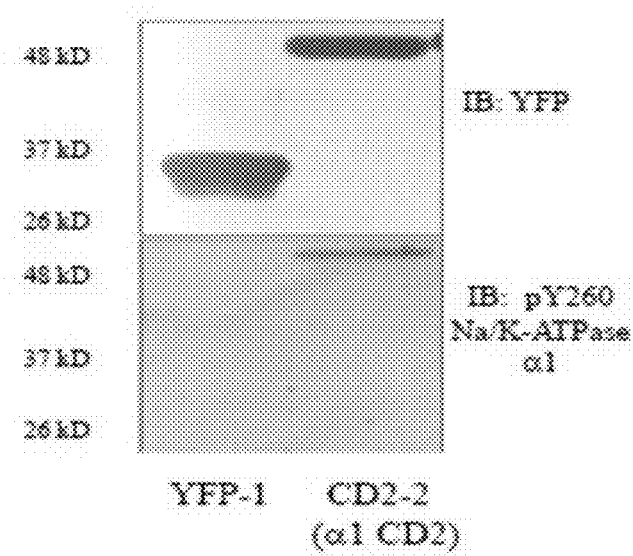
FIG. 4B

- NaSH2

Sequence - GRKKRRQRRRPPQSTNCVEGTARGIVVYTGD

- pNaSH2

Sequence - GRKKRRQRRRPPQSTNCVEGTARGIVV(pY)TGD where pY denotes phosphorylated tyrosine residue

CARDIOTONIC STEROID ANTAGONISTS AND RELATED METHODS

RELATED APPLICATION

This application claims priority from U.S. Provisional Application Ser. No. 61/974,252, filed Apr. 2, 2014, the entire disclosure of which is incorporated herein by this reference.

GOVERNMENT INTEREST

This invention was made with government support under grant number HL 109015 awarded by the National Institutes of Health. The government has certain rights in the invention.

TECHNICAL FIELD

The presently-disclosed subject matter relates to cardiotonic steroid antagonists and methods of using the same. In particular, the presently-disclosed subject matter relates to cardiotonic steroid antagonists comprising a peptide that functions as a Src SH2 domain antagonist of cardiotonic steroids and methods of using that peptide antagonist for the treatment of Src-associated diseases, such as cancer and cardiovascular disease.

BACKGROUND

Cardiotonic steroids are a group of compounds that bind to and inhibit Na/K-ATPase, a protein which is responsible for regulating ionic homeostasis. Newly emerging evidence suggests these compounds are synthesized in mammalian bodies and may regulate several important cellular processes in response to external stimulus. To date, however, the Na/K-ATPase still remains the only identified target for binding of cardiotonic steroids on a cell surface (Prassas and Diamandis 2008).

Na/K-ATPase is an ion transporting protein that pumps $Na^+$ and $K^+$ ions across the membrane. Besides ion pumping, a large number of Na/K-ATPases in the cell membrane can also form a receptor complex for cardiotonic steroids by directly interacting with Src kinase. Indeed, cardiotonic steroid binding can activate the bound Src kinase that in turn phosphorylates multiple protein kinases, stimulates ROS (Reactive Oxygen Species) production, alters intracellular calcium concentrations and thereby affects cell growth, proliferation and survival (Xie and Cal 2003). Moreover, endogenous cardiotonic steroids have a well-described role in regulating cardiovascular and renal functions. In this aspect, the signaling function of Na/K-ATPase is thought to be important as the circulating concentrations of endogenous cardiotonic steroids is extremely low and is unlikely to affect its ion pumping function. Deregulations in this signaling function results in cardiovascular as well as renal diseases and may also contribute to cancer cell growth. Therefore, there is a need for the development of molecules that are specifically targeted towards the inhibition of such cardiotonic steroid-mediated signal transduction (Bagrov, Shapiro et al. 2009).

Src kinase is a protein tyrosine kinase that is known to act as a mediator in many signaling pathways that regulate cellular properties. Deregulation of Src kinase is often associated with or known to be the causative agent for a variety of diseases including cancer and osteoporosis (Bolen, Veillette et al. 1987, Bromann, Korkaya et al. 2004, Brunton, Avizienyte et al. 2005). Currently, there are at least four Src kinase inhibitors (dasatinib, bosutinib, sarcatinib, and KX01) under development for cancer therapeutics. However, most of those inhibitors suffer from a lack of specificity, and thus, there is also a need for the development of Src-based inhibitors that are more specific in nature.

With further respect to the Src kinase, Src kinase comprises of a number of domains—a kinase domain that functions in phosphorylating other proteins and a SH2 and a SH3 domain that helps Src kinase to bind to signaling proteins and a unique region, in fact, Src kinase belongs to a large family of tyrosine kinases which share high degree of similarity in their kinase domain structure (Boggon and Eck 2004). As such, most inhibitors that are developed to target the Src kinase domain can also interact with other protein kinases nonspecifically, which, in turn, results in the observed loss of specificity. In contrast, however, the SH2 domain which serves the critical function of targeting Src kinase to signaling complexes for mediating protein-protein interaction tends to be highly specific (Songyang, Shoelson et al. 1993), and many intracellular signaling cascades, whose deregulation can cause diseases, rely on SH2 domain-mediated binding of Src kinase (Shvartsman, Donaldson et al. 2007), making the SH2 domain of Src a target for developing inhibitor molecules.

It is appreciated that SH2 domains recognize and bind preferably to phosphorylated tyrosine residues and the sequence surrounding the phosphotyrosine determines the specificity (Songyang and Cantley 2004). In fact, the selectivity for the tyrosine phosphorylation is so high that that residue is alone thought to confer about half of the binding energy. To date though, most SH2 domain inhibitors are still under development in in vitro systems in order to increase their efficacy under physiological conditions (Kraskouskaya, Duodu et al. 2013). In this context, a Src SH2 domain-directed specific antagonist of cardiotonic steroids would be both highly-desirable and beneficial as such an antagonist would be capable of: 1) antagonizing cardiotonic steroids; and 2) inhibiting Src-mediated signal transduction with a high level of selectivity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes cardiotonic steroid antagonists and methods of using the same. In particular, the presently-disclosed subject matter includes cardiotonic steroid antagonists that are comprised of a peptide that functions as a Src SH2 domain antagonist of cardiotonic steroids and methods of using that peptide antagonist for the treatment of Src-associated diseases, such as cancer and cardiovascular disease.

In some embodiments of the presently-disclosed subject matter, a cardiotonic steroid antagonist is provided in the form of a non-naturally occurring peptide. In some embodiments, the non-naturally occurring peptide comprises a tyrosine-phosphorylated fragment of the second cytoplasmic domain of a Na/K-ATPase α1 subunit. In some embodiments, the non-naturally occurring peptide comprises the sequence of SEQ ID NO: 1. In some embodiments, the non-naturally occurring peptide comprises a cell penetrating peptide operably linked to the peptide of SEQ ID NO: 1, such as, in certain embodiments, a HIV-TAT peptide, a penetratin peptide, a polyarginine peptide, a pep-1 peptide, and a transportin peptide. In some embodiments, the cell-penetrating peptide operably linked to the sequence of SEQ ID NO: 1 is a HIV-TAT peptide. In further embodiments, vectors are also provided that comprise a nucleic acid encoding a non-naturally occurring peptide having, the sequence of SEQ ID NO: 1 operably linked to an expression cassette for expression of the nucleic acid sequence encoding the amino acid sequence of SEQ ID NO: 1.

Also provided, in some embodiments of the presently-disclosed subject matter, are pharmaceutical compositions comprising a non-naturally occurring peptide having the sequence of SEQ ID NO: 1 and a pharmaceutically-acceptable vehicle, carrier, or excipient. In some embodiments, such pharmaceutical compositions further comprise an additional therapeutic agent, such as, in some embodiments, a chemotherapeutic agent, a toxin, an immunological response modifier, an enzyme, or a radioisotope. In some embodiments, the non-naturally occurring peptide is included in the composition in an amount sufficient to affect a cellular process selected from the group consisting of: antagonizing a cardiotonic steroid (CTS)-induced protein kinase cascade, upregulating a CTS induced protein kinase cascade; Src inhibition; Src stimulation; Na/K-ATPase mimic; Na/K-ATPase competitive inhibitor; Lyn inhibition; Lyn stimulation; ouabain antagonism; ouabain stimulation; ERK1/2 activation; ERK1/2 inhibition; membrane permeability by sodium ions; and membrane permeability by potassium ions. In some embodiments, the non-naturally occurring peptide included in the composition binds to Src with an IC50 of less than about 10 μM.

Further provided are methods of treating a Src-associated disease. In some embodiments, methods of treating an Src-associated disease are provided that comprise administering an effective amount of a non-naturally occurring, peptide comprising, the sequence of SEQ ID NO: 1 to a subject in need thereof. In some embodiments, the Src-associated disease is selected from the group consisting of cancer, vascular disease, cardiovascular disease, tissue fibrosis, and osteoporosis. In certain embodiments, the Src-associated disease is cancer, and the cancer is selected from prostate cancer, breast cancer, and neuroblastoma. In other embodiments, the Src-associated disease is cardiovascular disease, and the cardiovascular disease is selected from heart disease, cardiac hypertrophy, congestive heart failure, and ischemia-reperfusion injury. In some embodiments, the non-naturally occurring peptide used to treat the Src-associated disease comprises the sequence of SEQ ID NO: 3.

Still further provided, in some embodiments of the presently-disclosed subject matter, are methods for reducing Src activity in a cell. In some embodiments, a method for reducing Src activity in a cell is provided that comprises contacting a cell with an effective amount of a peptide comprising the sequence of SEQ ID NO: 1. In some embodiments, the cell is a monocyte, a heart cell, a liver cell, a vascular cell, a breast cell, a prostate cell, a kidney cell, a muscle cell, a brain cell, a bone cell, and/or a tumor cell. In some embodiments, the peptide of SEQ ID NO: 1, which contacts the cell, is operably linked to a cell-penetrating peptide.

Further features and advantages of the present invention will become evident to those of ordinary skill in the art after a study of the description, figures, and non-limiting examples in this document.

BRIEF DESCRIPTION OF THE DRAWINGS

FIG. 2A is an image showing the results of an experiment where five hundred of total cell lysate was immunoprecipitated with 10 μg anti-Src antibody and immunoprecipitates were subjected to Western blot analysis of YFP and Src. FIG. 2B is an image and a graph showing the results of an experiment where five hundred μg of total cell lysate was immunoprecipitated with 10 μg anti-Src antibody and analyzed for Na/K ATPase α1 co-imunoprecipitation. The values shown are mean±SEM from at least three independent experiments. **, p<0.01.

FIGS. 3A-3C includes images and graphs showing CD2 as a SH2 domain ligand. FIG. 3A includes images and a graphs showing the results of experiments where a yellow fluorescent protein (YFP) and CD2-2 expressing cells were grown up to 90% confluence, serum-starved overnight and total cell lysates were analyzed for pY418 Src and total Src, where a representative Western blot is shown and the data are mean±SEM of at least three independent experiments (*, p<0.05), and where, to ensure no clonal effect, CD2-1 another CD2 expressing cell line was also included. FIG. 3B includes a graph showing the results of a cell spreading assay where LLC-PK1 (untransfected), YFP and YFP-1, YFP-2 (YFP expressing control cells) and CD2-1, CD2-2, CD2-5 (YFP-CD2 expressing cells) were harvested using trypsin and 2×10$^5$ cells were plated in 6 cm dishes, where, at indicated time points, images of spreading cells were recorded using, phase contrast microscope and spread cells are defined as cells that were not round, had extended processes, and were not phase bright, and where the quantitative data are presented as mean±SEM of at least three independent experiments. **, p<0.01. FIG. 3C is an image showing expression of YFP and YFP-CD2 by different stable cell lines.

FIGS. 4A-4C include a schematic diagram and images relating to the phosphorylation of Y260 in CD2, FIG. 4A is a schematic diagram showing CD2 sequence from Na/K-ATPase α1 subunit with the tentative Src SH2 domain binding region surrounding Y260 marked in a box (SEQ ID NO: 10). FIG. 4B is an image showing the results of an experiment where five hundred μg of total cell lysate was immunoprecipitated with 10 μg anti-Src antibody and immunoprecipitates were subjected to Western blot analysis of tyrosine 260 phosphorylation using an anti-phosphotyrosine 260 Na/K-ATPase α1 antibody, and where the same membrane was stripped and probed for YFP. FIG. 4C includes images showing the results of an experiment where LLC-PK1 cells were grown up to 100% confluence and then serum starved overnight and treated with 100 nM ouabain for the indicated times and then western blotted by probing for pY260 α1 Na/K-ATPase and a 1 Na/K-ATPase, pV418 Src and total Src.

FIG. 5 is a schematic diagram showing the sequence of the unphosphorylated and phosphorylated cardiotonic steroid antagonist peptide of the presently-disclosed subject matter, where both the peptides are tagged with HIV-TAT sequence at the N terminus for facilitating cell penetration (SEQ ED NOS: 4 and 3, respectively).

FIG. 7A includes images and a graph showing the result of an experiment where serum starved cells were pre-incubated with or without indicated concentrations of different peptides and then exposed to 100 nM ouabain for 10 minutes and where cell lysates were then collected and analyzed for pERK/ERK. FIG. 7B includes images and a graph showing the results of experiments where cells were treated with 10 ng/ml of EGF and analyzed for ERK phosphorylation.

DESCRIPTION OF EXEMPLARY EMBODIMENTS

Figure 1:
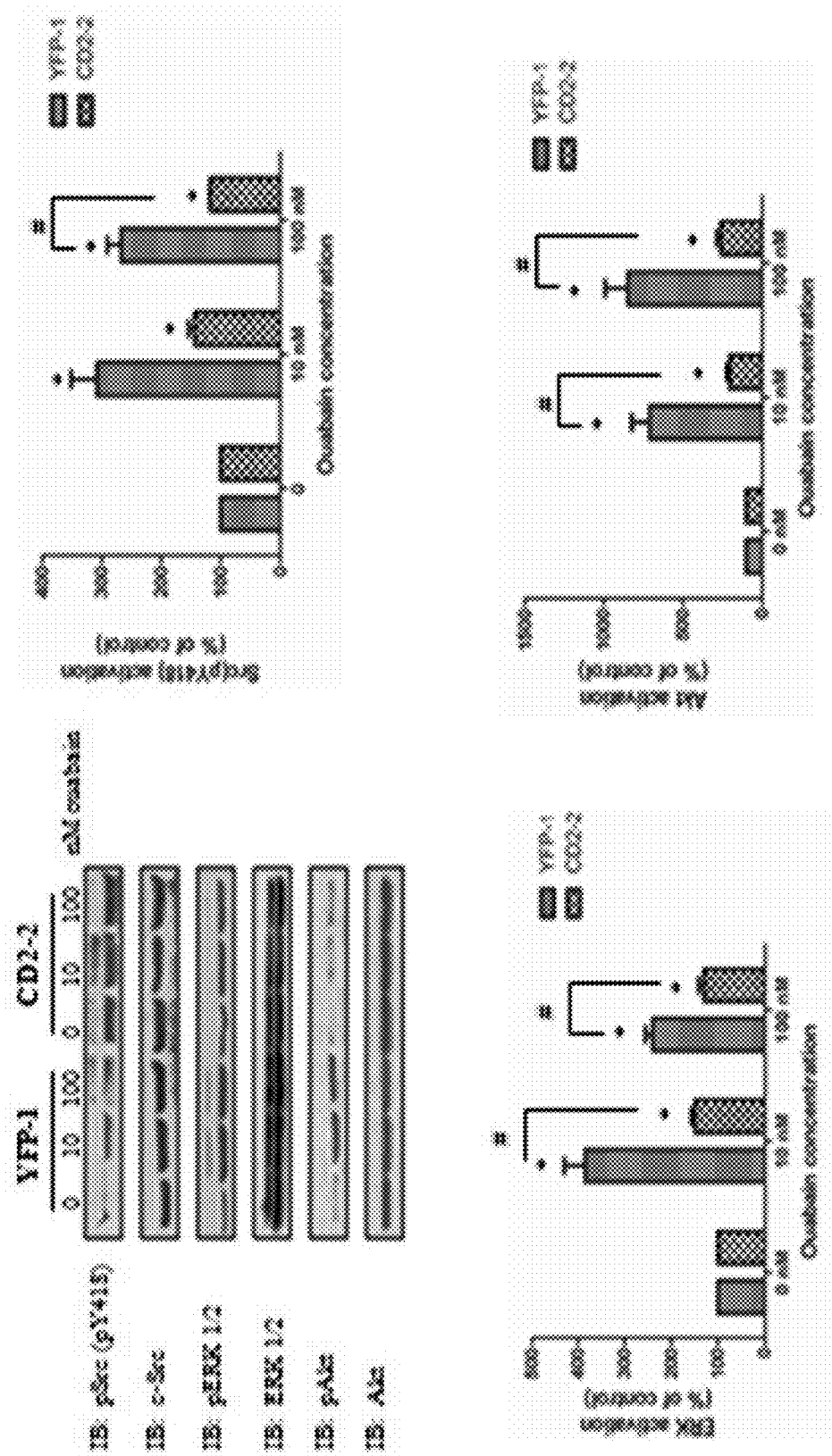
FIG. 1 includes images and graphs showing the effects of a peptide comprising the second cytoplasmic domain (CD2) of the Na/K-ATPase on ouabain mediated Src/ERK/Akt phosphorylation where cell lines were treated with indicated concentration of ouabain for 10 minutes, where cell lysates were collected and analyzed by western blots for pY418 Src and total Src, phospho-ERK1/2 and total ERK1/2, phospho-Akt and total Akt, and where the quantitative data shown are mean±SEM of at least three independent experiments (*p<0.05 compared with 0 nM control, #, p<0.05 compared with different cell lines).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

It is appreciated that the Na/K-ATPase acts as a regulator of Src kinase on the cell surface by binding to and inactivating a significant amount of Src kinase (Tian, Cai et al. 2006). One of the factors in this regulation is the interaction between CD2 (second cytoplasmic domain) of Na/K-ATPase and SH2 domain of Src. The SH2 domain functions in targeting Src kinase to its right binding partner in signaling pathways. In this regard, and without wishing to be bound by any particular theory or mechanism, it was believed that a SH2 domain-based inhibitor of Src kinase from CD2 of Na/K-ATPase should be capable of inhibiting Src-mediated signaling pathways specifically.

The presently-disclosed subject matter thus includes cardiotonic steroid antagonists and methods of using the same. In particular, the presently-disclosed subject matter relates to cardiotonic steroid antagonists comprising a peptide that functions as a Src SH2 domain antagonist of cardiotonic steroids, and methods of using that peptide antagonist for the treatment of Src-associated diseases, such as cancer and vascular disease. In some embodiments of the presently-disclosed subject matter, an isolated and non-naturally occurring polypeptide is provided that comprises the sequence of STNCVEGTARGIVV(pY)TGD [SEQ ID NO:

1] or conservative modifications of the sequence, where pY denotes a phosphorylated tyrosine residue that improves binding to the SH2 domain of Src kinase.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining am no acid sequence is usually identical to the corresponding positions in the reference polypeptide. Such deletions can occur at the amino-terminus or carboxy-terminus of the reference polypeptide, or alternatively both.

A fragment can also be a "functional fragment," in which case the fragment retains some or all of the activity of the reference polypeptide as described herein. For example, in some embodiments, a functional fragment of the amino acid sequence of SEQ ID NO: 1 retains some or all of the ability of the reference polypeptide to bind to the SH2 domain of Src kinase.

The terms "modified amino acid," "modified polypeptide," and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, a functional variant of the amino acid sequence of SEQ ID NO: 1 retains some or all of the ability of the reference polypeptide to bind to the SH2 domain of Src kinase with a high degree of specificity.

The term functional variant includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitutions, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine, or methionine for another; the substitution of one charged or polar (hydrophilic) residue for another such as between arginine and lysine, between glutamine and asparagine, between threonine and serine the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

The terms "isolated" or "non-naturally occurring" when used herein in the context of a nucleic acid or a polpeptide, is a nucleic acid or polypeptide that, by the hand of man, exists apart from its native environment and is therefore not a product of nature. An isolated and/or non-naturally occurring nucleic acid or polypeptide can exist in a purified form or can exist in a non-native environment such as, for example, in a transgenic host cell.

In some embodiments of the presently-disclosed subject matter, an isolated and non-naturally occurring polypeptide is provided that further comprises a cell penetrating peptide, such that the peptide of SEQ ID NO: 1 can be provided as part of a fusion peptide that is capable of entering a cell and binding to the SH2 domain of Src kinase. The term "fusion protein" is intended to describe at least two polypeptides, typically from different sources, which are operatively linked. With regard to the polypeptides, the term "operatively linked" is intended to mean that the two polypeptides are connected in a manner such that each polypeptide can serve its intended function. Typically, the two polypeptides are covalently attached through peptide bonds and can be produced by standard recombinant or chemical synthesis techniques. For example, using recombinant techniques, a DNA molecule encoding a first polypeptide can be directly ligated to another DNA molecule encoding the second polypeptide, and the resultant hybrid DNA molecule can be expressed in a host cell to produce the fusion protein. The DNA molecules are generally ligated to each other in a 5' to 3' orientation such that, after ligation, the translational frame of the encoded polypeptides is not altered (i.e., the DNA molecules are ligated to each other in-frame).

The term "cell-penetrating polypeptide" is used herein to refer to polypeptides that have the ability to provide entry of a coupled peptide into a cell. Exemplary cell-penetrating, polypeptides that can be used in accordance with the presently-disclosed subject matter include, but are not limited to: a human immunodeficiency virus transactivator of transcription (HIV-TAT) polypeptide (e.g., YGRKKRRQRRR (SEQ ID NO: 5) Frankel A. D., & Pabo, C. (1988), Cell, 55:1189-1193 Fawell, S., et al., (1994) PNAS USA, 91; 664-8; Becker-Hapak, M. et al. (2001), Methods, 24(3):247-56; Schwarze S. R. et al. (2000), Trends Cell Biol., 10(7):290-5; Matsushita, K. et al. (2005), Mol. Pharm., 67(4):1137-44; U.S. Pat. No. 6,645,501; and U.S. Patent Application Publication No. 2003/0040038); an Antennapedia homeodomain polypeptide, referred to as "penetratin" (e.g., AKIW-FQNRRMKWKKEN (SEQ ID NO: 6); Derossi et al., (1994), J. Bio. Chem., 269:10444-10450); an HSV VP22 polypeptide (Elliot and O'Hare. (1997), Cell. 88:223-234); a polvarginine polypeptide RRRRRRRRR; SEQ ID NO: 7); a pep-1 polypeptide (KETWWETWWTEWSQPKKKRKV; SEQ ID NO: 8); and a transportan polypeptide (GWTLN-SAGYLLGKINLIKALAALAKKIL; SEQ ID NO: 9) (Stewart et al., (2008), Org., Biomol. Chem. 6, 2242-2255). In some embodiments, the cell-penetrating polypeptide is a HIV-TAT polypeptide.

Further provided, in some embodiments of the presently-disclosed subject matter, are compositions (e.g. pharmaceutical compositions) comprising an amino acid sequence comprising at least ten amino acid residues of the sequence STNCVEGTARGIVV(pY)TGD [SEQ ID NO: 1] or conservative modifications of the sequence, where pY denotes the phosphorylated tyrosine residue to improve binding to SH2 domain of Src kinase. In some embodiments, the composition is capable of binding to Src with an IC50 of less than about 100 µM, 90 µM, 80 µM, 70 µM, 60 µM, 50 µM, 40 µM, 30 µM, 20 µM, or 10 µM. In some embodiments, the composition or amino acid sequence is included in the composition in an amount sufficient to affect a cellular process selected from the group consisting of antagonizing a CTS-induced protein kinase cascade; upregulating a CTS induced protein kinase cascade; Src inhibition; Src stimulation; Na/K-ATPase mimic; Na/K-ATPase competitive inhibitor; Lyn inhibition; Lyn stimulation; ouabain antagonism; ouabain stimulation; ERK1/2 activation; ERK1/2 inhibition; Akt stimulation; Akt activation; membrane permeability by sodium ions; membrane permeability by potassium ions.

In some embodiments, pharmaceutical compositions are provided that combine the peptides described herein with a pharmaceutically-acceptable vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition, as described herein, preferably comprises a composition that includes a pharmaceutical carrier, such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921, 5,603,956; 5,512,297; 5,399,362; 5,399,359; 5,399,358; 5,725,883; 5,773,025; 6,110,498; 5,952,004; 5,912,011; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying, agents (e.g. lecithin or acacia); note-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlomdifluoromethane, trichlorofluoromethane, dichlorotetrafluoroethane, carbon dioxide, or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt). The compositions can further be formulated as topical semi-sold ointment or cream formulations can contain a concentration of the presently-described compositions in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic. In some embodiments, such ointment or cream formulations can be used for trans-denial delivery of the pharmaceutical compositions described herein or for delivery to organs such as vagina or cervix in women.

Injectable formulations of the compositions can contain various carriers such as vegetable oils, dimethyl acetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

In some embodiments, the compositions described herein in addition to including a peptide of the presently-disclosed subject matter can also include at least one additional therapeutic agent. As used herein, the term "therapeutic agent" is used to refer to an agent that is capable of "treating" a disease, as defined herein below. In some embodiments, the therapeutic agent can comprise an agent that is useful to a treat a disease selected from the group consisting of: cancer; vascular disease; cardiovascular disease; heart disease; prostate cancer; breast cancer; neuroblastoma; cardiac hypertrophy; tissue fibrosis; congestive heart failure; ischemia/reperfusion injury; osteoporosis; and other Src-related diseases. In some embodiments, the additional agent is selected from the group consisting of: chemotherapeutic drug; a toxin; an immunological response modifier; an enzyme; and a radioisotope. For example, in some embodiments, other Src inhibitors, such as pNaKtide, can be used in conjunction with the pNaSH2 peptide (SEQ ID NO: 1) disclosed herein for the treatment of the above-mentioned diseases and disorders.

In some embodiments of the presently-disclosed subject matter, the therapeutic agent that is combined with a peptide of the presently-disclosed subject matter is a chemotherapeutic agent. Examples of chemotherapeutic agents that can be used in accordance with the presently-disclosed subject matter include, but are not limited to, platinum coordination compounds such as cisplatin, carboplatin or oxalyplatin; taxane compounds, such as paclitaxel or docetaxel; topoisomerase I inhibitors such as camptothecm compounds for example irinotecan or topotecan; topoisomerase II inhibitors such as anti-tumor podophyllotoxin derivatives for example etoposide or teniposide; anti-tumor vinca alkaloids for example vinblastine, cristine or vinorelbine; ani-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, Mass.); or YONDELIS® (Johnson & Johnson, New Brunswick, N.J.).

Further provided, in some embodiments, of the presently-disclosed subject matter, are methods for binding, a compound to the SH2 domain of Src. In some embodiments, a method for binding a compound to the SH2 domain of Src is provided that comprises contacting a compound herein to at least one SH2 domain of Src. In some embodiments, the methods include binding a compound to the SH2 domain of Src in a Src-expressing cell by contacting a compound described herein to at least one Src-expressing cell. In some embodiments, the Src-expressing cell is a mammalian cell, such as a monocyte, heart cell, liver cell, vascular cell, breast cell, prostate cell, kidney cell, muscle cell, blood cell, brain cell, or bone cell.

Still further provided, in some embodiments of the presently-disclosed subject matter, are methods of treating a Src-associated disease in a subject in need of such treatment. In some embodiments, a method of treating a Src-associated disease is provided that comprises administering an effective amount of a composition described herein (e.g., a peptide having the sequence of SEQ ID NO: 1) to a subject in need of such treatment. As used herein, the terms "treatment" or "treating" relate to any treatment of a condition of interest (e.g., a cancer), including therapeutic treatment. As such, the terms "treatment" or "treating" include, but are not limited to: inhibiting the progression of a condition of interest; arresting the further development of a condition of interest; reducing the severity of a condition of interest; ameliorating or relieving symptoms associated with a condition of interest; and causing a regression of a condition of interest or one or more of the symptoms associated with a condition of interest in a subject.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels, and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments, the Src-associated disease is selected from the group consisting of cancer, vascular disease, cardiovascular disease, tissue fibrosis, and osteoporosis. In some embodiments, the Src-associated disease is cardiovascular disease, and the cardiovascular disease is selected from the group consisting of heart disease, cardiac hypertrophy, congestive heart failure, and ischemia-reperfusion injury.

In some embodiments, the Sri-associated disease is cancer. In some embodiments, treating a cancer can include, but is not limited to, killing cancer cells, inhibiting the development of cancer cells, inducing apoptosis in cancer cells, reducing the growth rate of cancer cells, reducing the incidence or number of metastases, reducing tumor size, inhibiting tumor growth, reducing the available blood supply to a tumor or cancer cells, promoting an immune response against a tumor or cancer cells, reducing or inhibiting the initiation or progression of a cancer, or increasing the lifespan of a subject with a cancer.

As used herein, the term "cancer" refers to all types of cancer or neoplasm or malignant tumors found in animals, including leukemias, carcinomas, melanoma, and sarcomas. By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholanciocellular carcinoma, chorionic carcinoma, colloid carcinoma, comedo carcinoma, corpus carcinoma, cribriform carcinoma, carcinoma en cuirasse, carcinoma Butane cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcthom carcinoma gigantocellulare, glandular carcinoma, granulosa cell carcinoma, hair-matrix carcinoma, Nematoid carcinoma, hepatocellular carcinoma. Hurthle cell carcinoma, hyaline carcinoma, hypemephrord carcinoma, infantile embryonal carcinoma, carcinoma in situ, intraepidermal carcinoma, intraepithelial carcinoma, Krompecher's carcinoma, Kulchitzky-cel carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangieciaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma. Abernethy's sarcoma, adipose sarcoma, liposarcoma, alveolar soft part sarcorna, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma. Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, anaiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tuna for arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, nivel-tile melanoma, lentigo maligna melanoma, malignant melanoma, nodular melanoma subungal melanoma, and superficial spreading, melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insuhmoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of prostate cancer, breast cancer, and neuroblastoma.

For administration of a therapeutic composition as disclosed herein, conventional methods of extrapolating human dosage based on doses administered to a muriate animal model can be carried out using the conversion factor for converting the mouse dosage to human dosage: Dose Human per kg=Dose Mouse per kg×12 (Freireich, et a (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different annual species as described by Freireich, et al. (Freireich et al., (1966) Cancer Chemother Rep. 50:219-244). Briefly, to express a mg/kg dose in any given species as the equivalent mg/sq in dose, multiply the dose by the appropriate kg, factor. In an adult human, 100 mg/kg is equivalent to 100 mg/kg×37 kg/sq m=3700 mg/m2.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administrationdermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally, intravenously, intranasally, or intraperitoneally to thereby treat a disease or disorder.

Regardless of the route of administration, the compositions of the presently-disclosed subject matter typically not only include an effective amount of a therapeutic agent, but are typically administered in amount effective to achieve the desired response. As such, the term "effective amount" is used herein to refer to an amount of the therapeutic composition (e.g., a peptide of SEQ ID NO: 1 and a pharmaceutically vehicle, carrier, or excipient) sufficient to produce a measurable biological response (e.g., an increase in Src inhibition). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Herkow et al., (1997) The Merck Manual of Medical Information, Home ed. Merck. Research Laboratories, Whitehouse Station, N.J.; Goodman et al., (1996) Goodman & Gilman's the Pharmacological Basis of Therapeutics, 9th ed, McGraw-Hill Health Professions Division, N.Y.; Ebadi, (1998) CRC Desk Reference of Clinical Pharmacology. CRC Press, Boca Raton, Fla.; Katzung (2001) Basic & Clinical Pharmacology, 8th ed. Lange Medical Books/McGraw-Hill Medical Pub. Division, N.Y.; Remington et al., (1975) Remington's Pharmaceutical Sciences, 15th ed. Mack Pub. Co., Easton, Pa., and Speight et al., (1997) Avery's Drug Treatment: A Guide to the Properties, Choice, Therapeutic Use and Economic Value of Dines in Disease Management, 4th ed., Adis International, Auckland/Philadelphia; Duch et al., (1998) Toxicol. Lett 100-101:255-263.

By virtue of the binding affinity of the peptides described herein to the SH2 domain of Src, in some embodiments, methods for reducing Src activity in a cell can also be provided that comprise the step of contacting a cell with an effective amount of a Src-inhibiting peptide described herein e.g., a peptide of SEQ ID NO: 1). In some embodiments, the cell is selected from the group consisting of a monocyte, a heart cell, a liver cell, a vascular cell, a breast cell, a prostate cell, a kidney cell, a muscle cell, a brain cell, and a tumor cell. In some embodiments, embodiments, by contacting a cell with a composition described herein, the composition affects Focal Adhesion Kinase (FAK) activity in the cell (e.g., a tumor cell), reduces reducing tumor cell migratiin, kills cancer cells when the expression of Na/K ATPase is reduced, inhibits cell growth in a tumor cell, inhibits prostate tumor cell growth, inhibits breast tumor cell growth, or affects: Src binding; Src inhibition; Src stimulation; Src function; Lyn binding; Lyn function; Lyn inhibition; ouabain antagonism; Na/K-ATPase function; ERK1/2 functions; FAK inhibition; membrane permeability by sodium ions; and membrane permeability by potassium ions.

Various methods known to those skilled in the art can be used to assess the foregoing effects. Furthermore, although certain embodiments of the methods disclosed herein only call for a qualitative assessment (e.g., the presence or absence of Src inhibition), other embodiments of the methods call for a quantitative assessment (e.g., an amount of Src inhibition in a subject or a cell or tissue of the subject). Such quantitative assessments can be made, for example, using any number of methods, as will be understood by those skilled in the art.

With respect to the administration of or the contacting of a cell with the compositions described above to reduce an amount of Src activity, the terms "reduce," "reducing," or "reduction" when used herein in reference to Src activity are used to refer to any decrease of suppression in the amount or rate of Src activity. Of course, it is understood that the degree of reduction need not be absolute (i.e., the degree of inhibition need not be a complete prevention of Src activity) and that intermediate levels of a reduction in Src activity are contemplated by the presently-disclosed subject matter. As such, in some embodiments, the reduction in Src activity can be about 5%, about 10%, about 15%, about 20%, about 25%, about 30%, about 35%, about 40%, about 45%, about 50%, about 55%, about 60%, about 65%, about 70%, about 75%, about 80%, about 8.5%, about 90%, about 95%, or about 99%.

The skilled artisan will also understand that measuring a reduction in the amount of a certain feature (e.g., Src inhibition) or an improvement in a certain feature (e.g., tumor size) in a subject is a statistical analysis. For example, an increase in an amount of Src inhibition in a subject can be compared to control level of Ste activity, and an Sri: inhibition of less than or equal to the control level can be indicative of a reduction in the amount of Src activity, as evidenced by a level of statistical significance. Statistical significance is often determined by comparing two or more populations, and determining a confidence interval and/or a p value. See, e.g., Dowdy and Wearden, Statistics for ResearchTohn Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

The practice of the pr s ntly-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. S. Gait, ed., 1984; Nucleic Acid Hybridization, D. Hames & S. J. Higgins, eds., 1984; Transcription and Translation, B. D. Flames & S. J. Higgins, eds., 1984; Culture Of Animal Cells, R. I. Freshney, Alan R. Liss, Inc., 1987; Immobilized Cells And Enzymes, IRL Press, 1986: Perbal (1984), A Practical Guide To Molecular Cloning; See Methods In Enzymology (Academic Press, Inc., N.Y.); Gene Transfer Vectors. For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental tmmunology, Volumes I-IIV, D. M. Weir and C. C. Blackwell, eds., 1986.

The presently-disclosed subject matter is further illustrated by the following specific but non-limiting examples.

EXAMPLES

Example 1

Second Cytoplasmic Domain of Na/K-ATPase as a Regulator of Src SH2 Domain

Figure 2A:
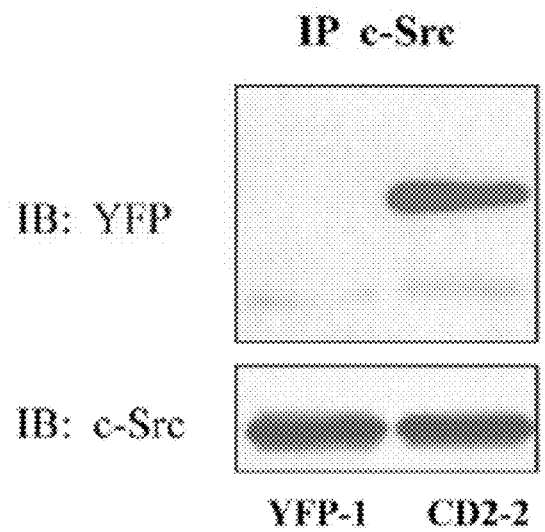
FIGS. 2A-2B include images and graphs showing the interaction of CD2 with Src.
Figure 2B:
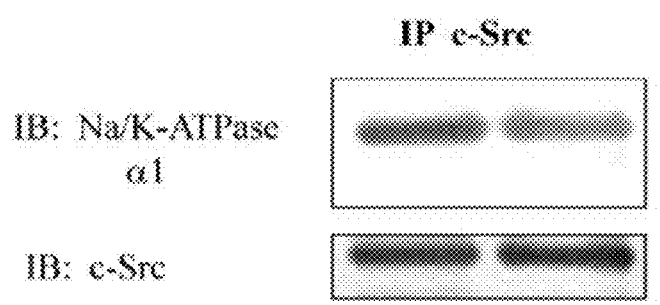
Figure 2B:
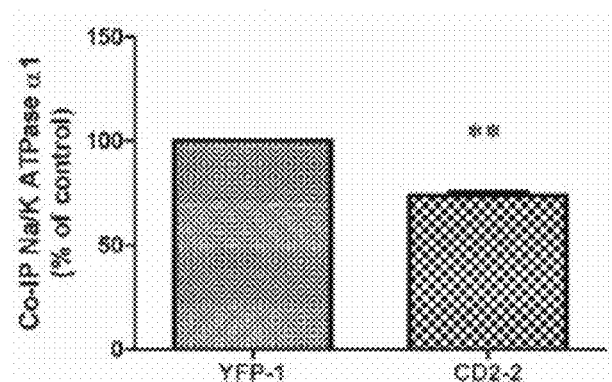

The Na/K-ATPase interacts with Src kinase directly by two domain-domain interactions (Tian, Cai et al, 2006, Ye, Li et al. 2011), Specifically, the second cytoplasmic domain (CD2) of the Na/K-ATPase binds the Src SH2 domain and the N domain of the Na/K-ATPase binds the Src kinase domain. The binding of cardiotonic steroids, such as ouabain, disrupts the N domainlinase domain interaction, whereas the CD2/SH2 interaction is generally constitutive. In this regard, since the CD2 binds the Src SH2 domain and the SH2 domain functions in targeting Src kinase to specific signaling complexes, it was believed that ectopically expressed CD2 would act as a dominant-negative mutant of the Na/K-ATPase/Src receptor complex in cells and thereby inhibit ouabain-mediated cell signaling. To test that belief, CD2 was expressed in LLC-PK1 cells as a yellow fluorescent protein (YFP) fused protein and a YFP expressing cell line was used as a control. From these experiments, it was demonstrated that CD2 could inhibit ouabain-mediated protein phosphorylation in cells (FIG. 1) by binding to Src kinase (FIG. 2A) and preventing Src Kinase from being targeted to the Na/K-ATPase (FIG. 2B). Those studies confirmed the validity of CD2/SH2 interaction, and also indicated a role for CD2-mediated regulation of Src kinase through the Src SH2 domain in cellular physiology.

Figure 3A:
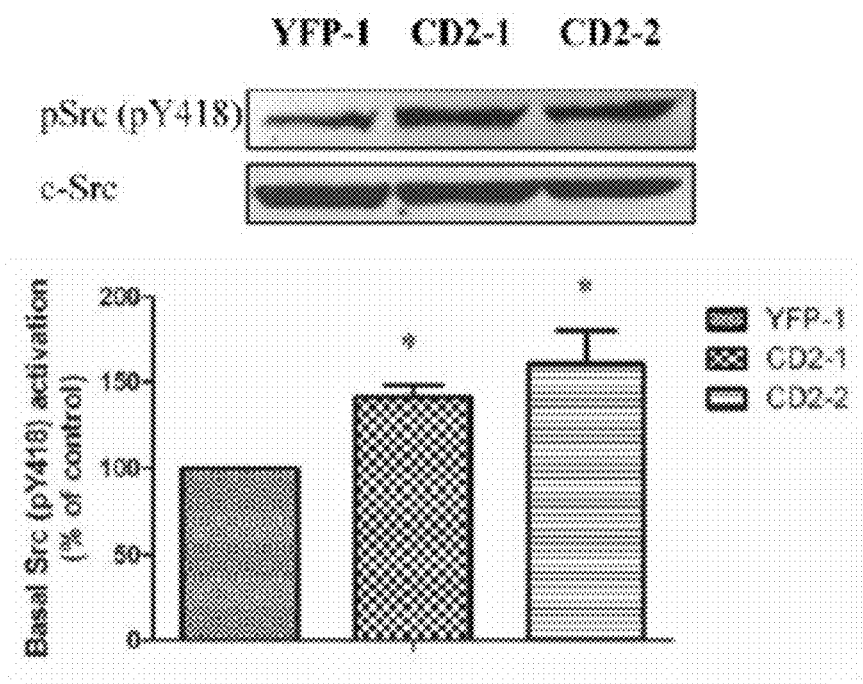

To further clarify the function of CD2 as a SH2 domain inhibitor, whether CD2 acts as a SH2 domain ligand in cells was next examined. It is appreciated that SH2 domain ligands can increase the basal Src activity by displacing its intra-molecular regulation (Liu, Brodeur et al. 1993, Yadav and Miller 2007). In this regard, if CD2 behaves like a SH2 domain ligand in cells, it should increase basal Src activity measured as Y418 phosphorylation. As depicted in FIG. 3A, it was determined that CD2 expression does increase basal Src activity in this manner as compared with a control cell line.

Figure 3B:
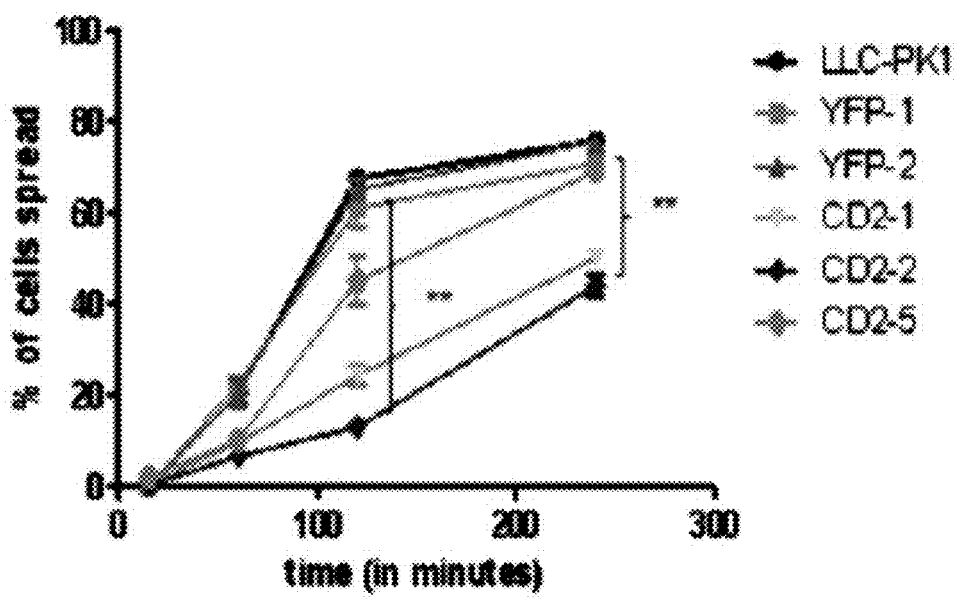

It is also appreciated that cell spreading is a process by which cells attach in their normal tissue microenvironment, and studies have shown that cell spreading is dependent on the SH2 domain of Src kinase (Kaplan, Swedlow et al. 1995). In this regard, it was next investigated whether CD2 can regulate cell spreading by acting as a SH2 domain inhibitor in cells. Upon analysis of the results from those experiments, it was determined that expression of CD2 was capable of inhibiting Src-mediated cell spreading (FIG. 3B) in a dose-dependent manner (FIG. 3C). Thus, the above studies confirmed the role of CD2 as SH2 domain-specific ouabain/cardiotonic steroid antagonist.

Example 2

Development of Peptide Antagonist for Disruption of CD2/SH2 Interaction

Figures 4C, 5:
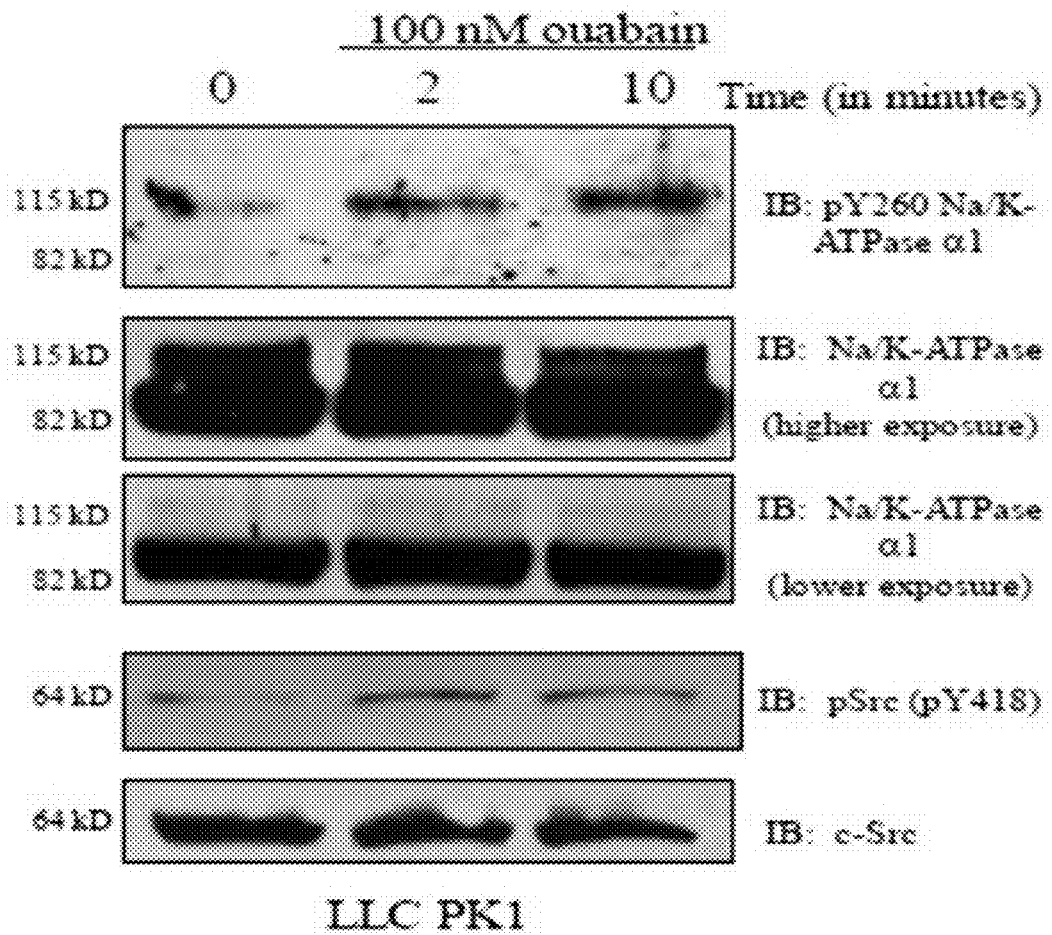

In view of the foregoing findings, experiments were then undertaken to develop a highly specific peptide antagonist for disrupting the CD2/SH2 interaction in order to inhibit the cardiotonic steroid-mediated signaling, in cells. Src SH2 domains have been observed to display a preference in binding phosphorylated tyrosine residues. As shown in FIG. 4A, CD2 from Na/K-ATPase α1 subunit (mammalian; SEQ ID NO:) contains only a single tyrosine at position 260 (in unmodified Na/K-ATPase), so an experiment was performed to determine if that tyrosine could be phosphorylated CD2 expressing cells. As depicted in FIG. 4B, CD2 was capable of being phosphorylated when it was expressed in cells. FIG. 4C further shows that in normal LLC-PK1 cells, tyrosine 260 of full length Na/K-ATPase was phosphorylated. Moreover, that phosphorylation could be stimulated by ouabain, as ouabain increased the phosphorylation in a time-dependent manner. These findings thus indicated that the tyrosine 260 can indeed be phosphorylated in normal cells and may be an important factor for SH2 domain binding in the target peptide. It is also important to note that non-phosphorylated CD2 could also bind Src SH2, as was previously demonstrated, with high affinity (Tian, Cai et al. 2006, Ye, Li et al. 2011). Thus, it was conceivable that pY260 CD2 could have a much higher binding affinity to Src SH2, making the CD2-derived phospho-peptide a more effective Src SH2 inhibitor as well as a better antagonist of cardiotonic steroids.

Example 3

Affinity of Peptide Antagonist

It was previously demonstrated that a peptide derived from CD2 called CD2C2 (see, e.g., SEQ ID NO: 1 in PCT Application No. PCT/US2011/021130, which is incorporated herein by reference) is an effective ouabain antagonist when assayed using a reconstituted in vitro system. In view of the above new findings and the previous information regarding CD2C2, experiments were subsequently undertaken to assess whether the same peptide with Y260 being phosphorylated (see SEQ ID NO: 1 of the present application) has a higher affinity than. CD2C2 (see SEQ ID NO: 2 of the present application). Briefly, to perform these experiments, and in order to make the peptide cell membrane permeable, the peptide of SEQ ID NO: 1 was attached to a TAT tag as done previously with other Na/K-ATPase-derived peptides (Li, Cai et al. 2009). The new peptide was designated pNaSH2 (SEQ ID NO: 3). To compare and contrast, CD2C2 was also synthesized with the same TAT tag, and was designated as NaSH2 (SEQ ID NO: 4) to indicate that the peptide was not phosphorylated at Y260. The sequences and names of these peptides are shown in FIG. 5.

Figure 6:
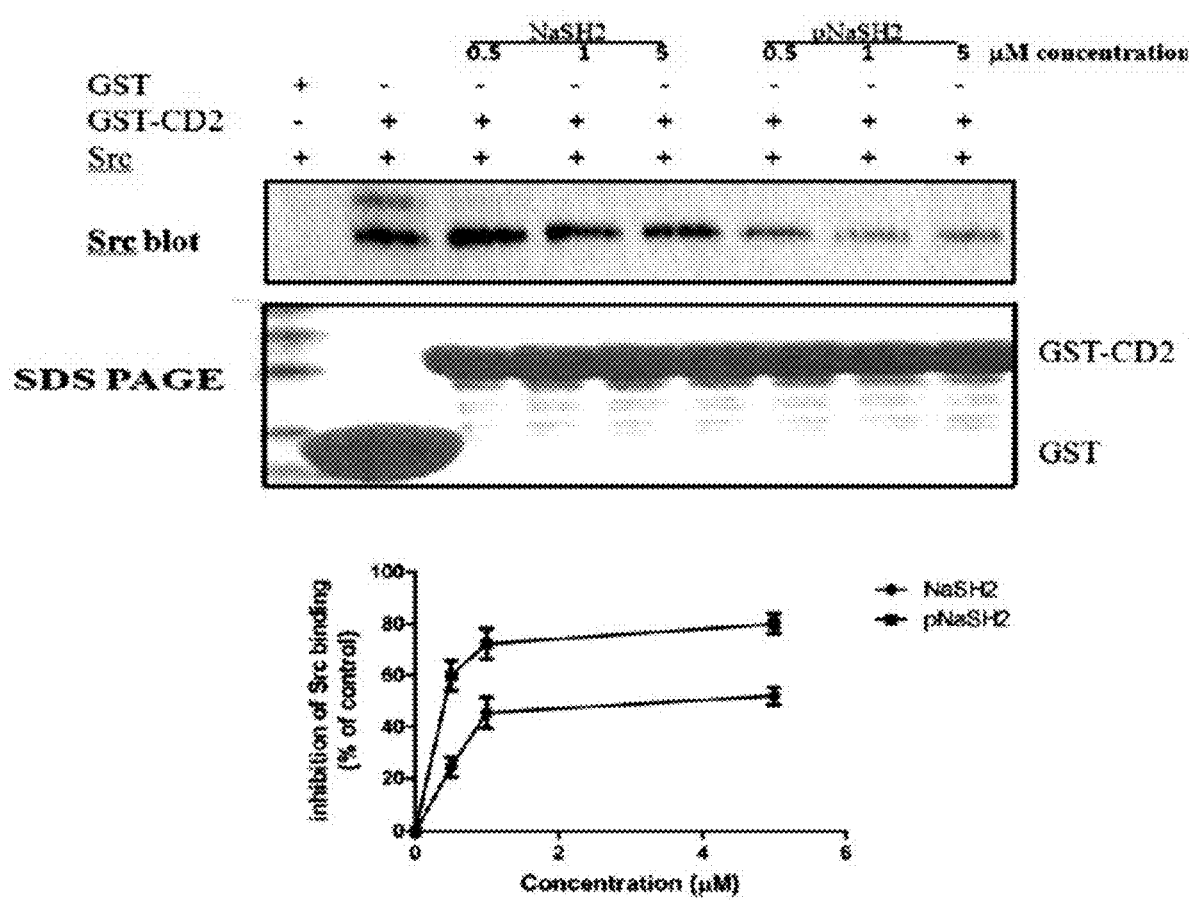
FIG. 6 includes images and a graphs showing the effects of developed peptides on CD2/SH1 interaction, where one unit of purified Src was incubated with indicated concentrations of peptides for one hour and then glutathione bead bound GST-CD2 was used to pull down available Src, and where the bound Src was then resolved by SDS-PAGE, transferred to nitrocellulose membrane and probed with a Src specific antibody. The upper panel of FIG. 6 shows the amount of Src precipitated, whereas the lower panel of FIG. 6 shows the amount of GST bound protein used for each condition (SDS-PAGE image).

To assess the effectiveness of the phosphotylated peptide (pNaSH2) versus the non-phosphorylated peptide (NaSH2), in vitro peptide inhibition assays were then performed. Briefly, purified human recombinant Src was incubated with different concentrations of both the peptides for 30 min. Glutathione bead bound GST-CD2 was then added to the reaction and incubated for 1 hour. The GST pull down pellets were then analyzed for bound Src using an anti-Src antibody. As shown in FIG. 6, pNaSH2 was more potent and effective than NaSH2 in blocking CD2/Src interaction.

Figures 7A, 7B:
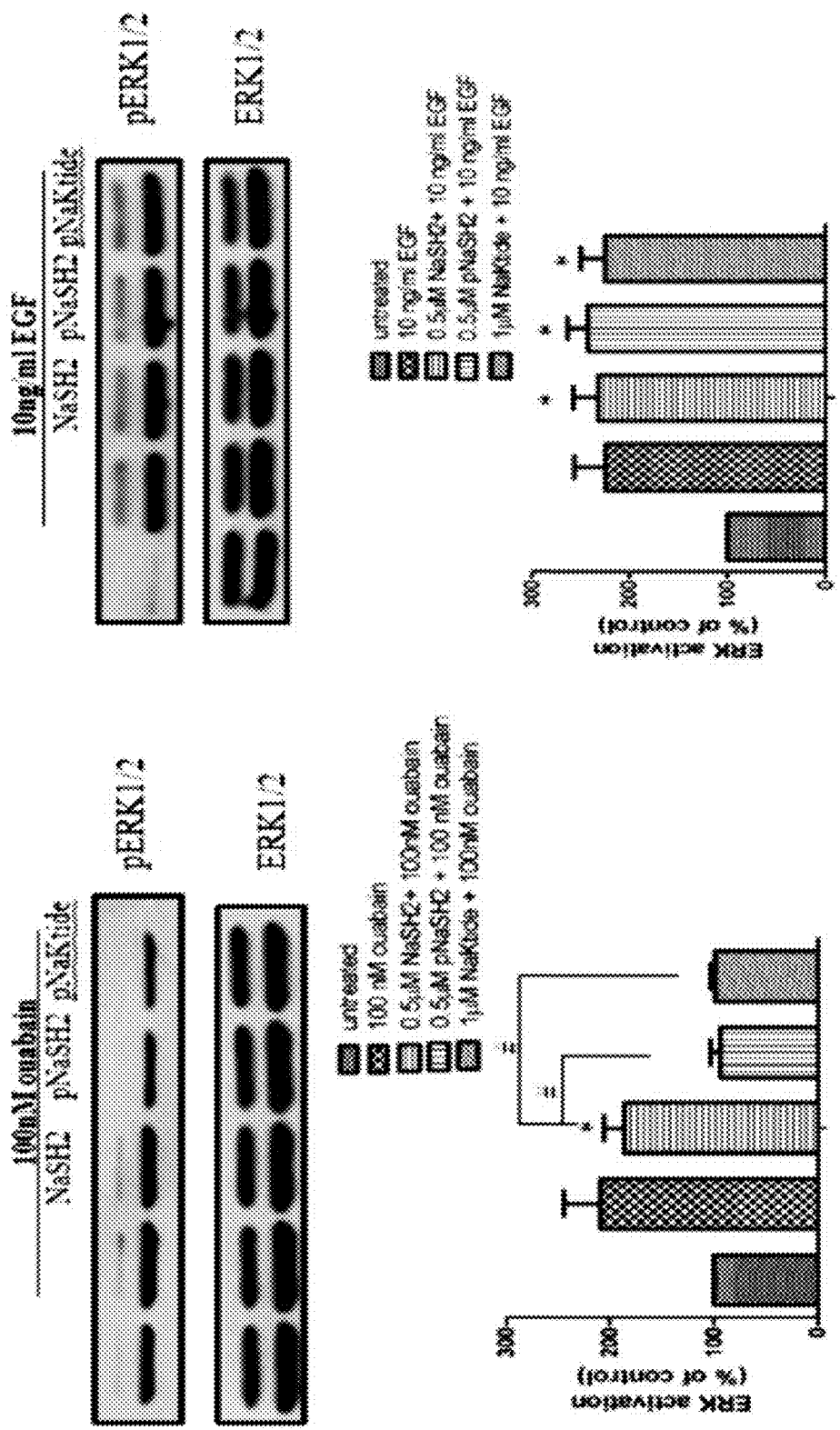
FIGS. 7A-7B include images and graphs showing, the effects of pNaSH2 (SEQ ID NO: 3) on ouabain signaling.
Figure 8:
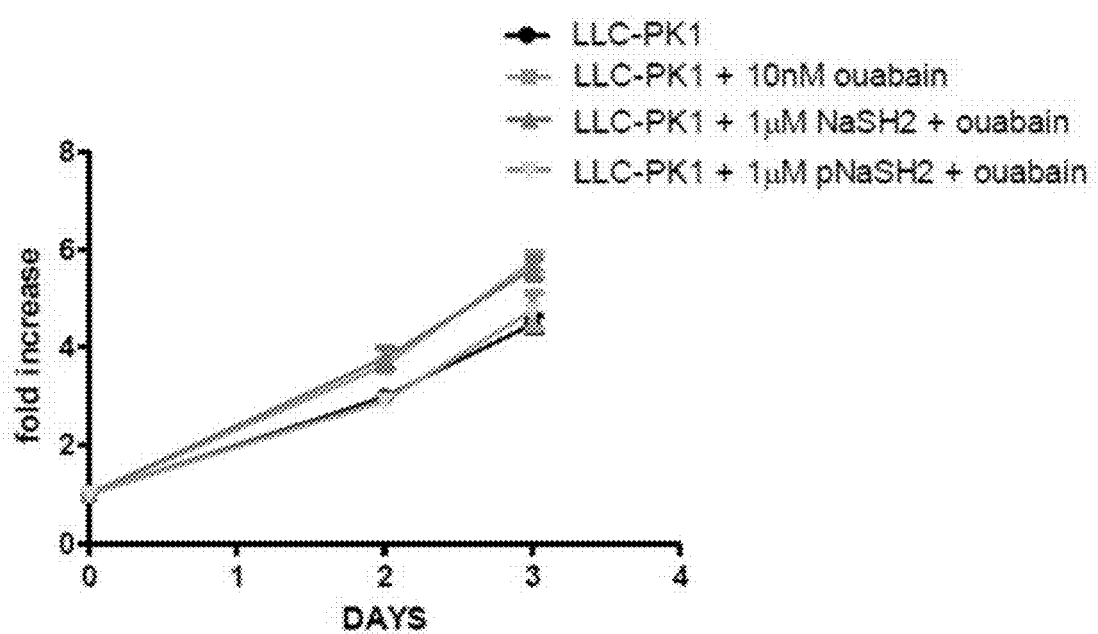
FIG. 8 is a graph showing the effects of pNaSH2 (SEQ ID NO: 3) on ouabain-mediated cell proliferation where cells (20,000) were plated in triplicates in 12 well plates, allowed to grow for 24 hours and then serum starved for 24 hours, where the cells were pretreated with 1 μM concentration of indicated peptides and then stimulated with 10 nM ouabain, and where, at indicated time points, cell numbers were counted using a hemocytometer chamber (*, p<0.05 compared with no treatment and #, p<0.05 compared with ouabain treated (no peptide inhibition)).
Figure 9:
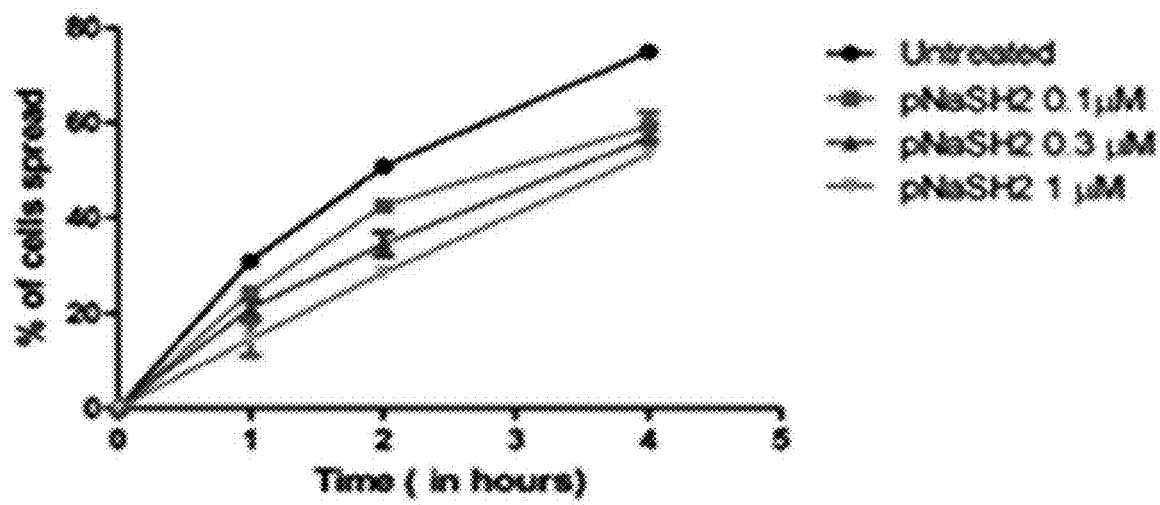
FIG. 9 includes graphs showing the effects of pNaSH2 (SEQ ID NO: 3) on cell spreading where LLC-PK1 cells were pre-incubated with indicated concentrations of different peptides for one hour and the cells were harvested and plated for cell spreading as described above with reference to FIG. 3.
Figure 9:
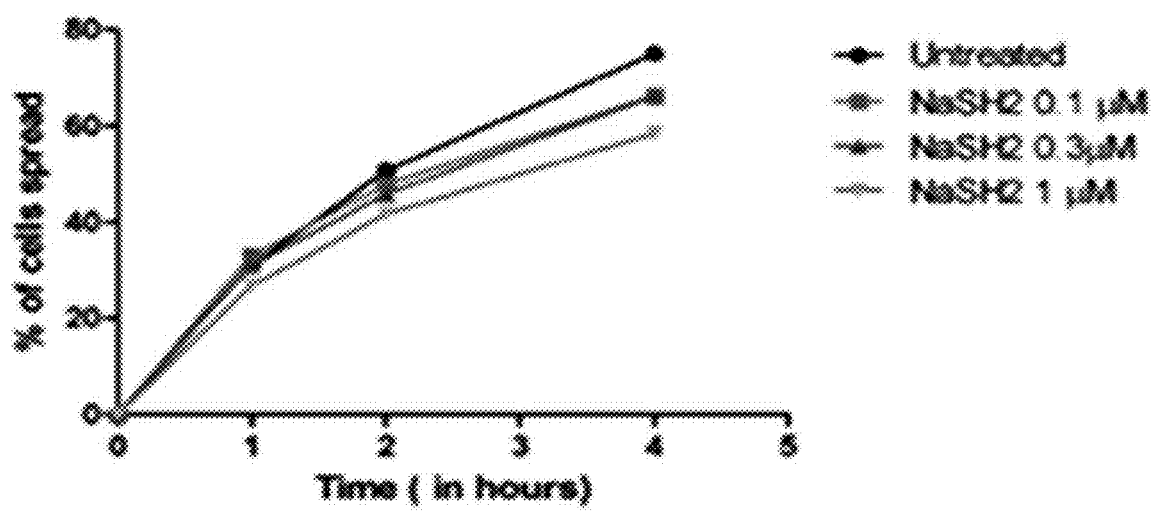

According to the previous dataset, if pNaSH2 is capable of blocking CD2/SH2 interaction it should also antagonize ouabain-mediated ERK phosphorylation in cells. In this regard, LLC-PK1 cells were then preheated with either 0.5 µM of NaSH2 or pNaSH2 and 1 µM pNaKtide (positive control) for 1 hour. The cells were then stimulated with 100 nM ouabain for 10 minutes and assayed for phosphorylated ERK by Western blot. As shown in FIG. 7A, pNaSH, but not NaSH2, completely abolished ouabain-induced ERK phosphorylation. In contrast, none of the peptides were able to inhibit EGF mediated ERK phosphorylation (FIG. 7B), indicating that the effect of pNaSH2 was specific to the ouabain-mediated signaling pathway, Ouabain can also stimulate cell proliferation of LLC-PK1 cells at very low concentrations (Tian, Li et al. 2009). Therefore, as an ouabain antagonist, it was believed that pNaSH2 should be able to inhibit ouabain-mediated cell proliferation. As depicted in FIG. 8, pNaSH2 did in fact inhibit ouabain-induced cell proliferation, while NaSH2 was ineffective at the concentration utilized. Furthermore, to assess whether pNaSH2 was effective in acting as a Src SH2 inhibitor, its effect on cell spreading was also measured. As depicted in FIG. 9, pNaSH2 was more effective in the inhibition of cell spreading.

Taken together the above studies indicate that presence of a phosphorylated tyrosine increases the effectiveness of the CD2-derived peptide by making it a more efficient and specific ouabain antagonist as well as a Src SH2 inhibitor. Those properties of pNaSH2 (the dual functionalities) and high effectiveness of pNaSH2 make the peptide unique in comparison with other developed SH2 inhibitors reported in the literature. In vitro competition analyses indicated that pNaSH2 has an $IC_{50}$ of about 0.5 µM in comparison to about 6.5 µM with the best SH2 inhibitory peptide pYEEI discovered so far (Kraskouskaya, Duodu et al. 2013). Further, it was believed that the above experiments show for the first time that pNaSH2 is as effective as SH2 inhibitors in cells at concentration of 1 µM. Finally, it was believed that in light of those properties, the practical usefulness of pNaSH2, in comparison to NaSH2, was greater even though both may block ouabain signaling and act as a SH2 inhibitor. That increased effectiveness made it possible for the use of pNaSH2 as an experimental tool as well as for further development of new therapeutics.

Throughout this document, various references are mentioned. All such references are incorporated herein by reference, including the references set forth in the following list:

REFERENCES

1. Bagrov, A. Y., J. I. Shapiro and O. V. Fedorova (2009). "Endogenous cardiotonic steroids: physiology, pharmacology, and novel therapeutic targets." Pharmacol Rev 61(1): 9-38.
2. Boggon, T. J. and M. J. Eck (2004). "Structure and regulation of Src family kinases." Oncogene 23(48): 7918-7927.
3. Bolen, T. B., Veillette, A. M. Schwartz, V. DeSeau and N. Rosen (1987). "Activation of pp60c-src protein kinase activity in human colon carcinoma." Proc. Natl Acad Sci USA 84(8): 2251-2255.
4. Bromann, P. A., Korkaya and S. A. Courtneidae (2004). "The interplay between Src family kinases and receptor tyrosine kinases." Oncogene 23(48): 7957-7968.
5. Brunton, V. G., E. Avizienyte, V. J. Fincharn, B. Serrels, C. A. Metcalf, 3rd, T. K. Sawyer and M. C. Frame (2005). "Identification of Src specific phosphorylation site on focal adhesion kinase: dissection of the role of Src SH2 and catalytic functions and their consequences for tumor cell behavior." Cancer Res 65(4): 1335-1342.
6. Kaplan, K. B., J. R. Swedlow, D. O. Morgan and H. E. Varmus (1995). "c-Src enhances the spreading of src-/- fibroblasts on fibronectin by a kinase-independent mechanism." Genes Dcv 9(12): 1505-1517.
7. Kraskouskaya, D., E. Duodu, C. C. Arpin and P. T. Gunning (2013), "Proaress towards the development of SH2 domain inhibitors." Chem Soc Rev 42(8): 3337-3370.
8. Li, Z., T. Cai, J. Tian, S. X. Xie, X. Zhao, L. Liu, J. I. Shapiro and Z. Xie (2009). "NaKtide, a Na/K-ATPase-derived peptide Src inhibitor, antagonizes ouabain-activated signal transduction in cultured cells." J Biol Chem 284(31): 21066-21076.
9. Liu, X., S. R. Brodeur, G. Gish, Z. Sougyang, L. C. Cantley, A. P. Laudano and T. Pawson (1993), "Regulation of c-Src tyrosine kinase activity by the Src SH2 domain," Oncogene 8(5): 1119-1126.
10. Prassas, I. and E. P. Diamandis (2008). "Novel therapeutic applications of cardiac glycosides." Nat Rev Drug Discov 7(11): 926-935.
11. Shvartsman, D. E. J. C. Donaldson, B. Diaz. O. Gutman, G. S. Martin and Y. I. Henis (2007). "Src kinase activity and SH2 domain regulate the dynamics of Src association with lipid and protein targets." J Cell Biol 178(4): 675-686.
12. Songyang. Z. and L. C. Cantley (2004). "ZIP codes for delivering SH2 domains." Cell 116(2 Suppl): S41-43, 42 p following S48.
13. Songyang. Z., S. E. Shoelson, M. Chaudhuri, O. Gish, T. Pawson, W. G. Haser, F. King, T. Roberts, S. Ratnofsky, R. I. Lechleider and et al. (1993). "SH2 domains recognize specific phosphopeptide sequences." Cell 72(5): 767-778.
14. Tiari, J., T. Cai, Z. Yuan, H. Wang, L. Liu, M. Haas, E. Maksimova, X. Y. Huang and Z. J. Xie (2006). "Binding of Src to Na+/K+-ATPase forms a functional signaling complex." Mol Biol Cell 17(1): 317-326.

15. Thin, J., X. Li, M., Liang, L. Liu, X. Xie, Q. Ye, P. Kometiani, M. Tillekeratne R. Jin and Z. Xie (2009). "Changes in sodium pump expression dictate the effects of ouabain on cell growth." J Biol Chem 284(22): 14921-14929.
16. Xie, Z. and T. Cai (2003). "Na+-K+-ATPase-mediated signal transduction: from protein interaction to cellular function." Mol Inter 3(3): 157-168.
17. Yadav, S. S. and W. T. Miller (2007). "Cooperative activation of Src family kinases by SH3 and SH2 ligands." Cancer Lett 257(1): 116-123.
18. Ye, Q., Z. Li, J. Tian, I. X. Xie. L. Liu and Z. Xie (2011), "Identification of a potential receptor that couples ion transport to protein kinase activity." J Biol Chem 286(8): 6225-6232.
19. International Patent Application Publication No. WO 2011/088210, filed Jan. 13, 2011 and entitled "Materials and Methods Related to Sodium/Potassium Adenosine Triphosphatase and Src."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A non-naturally occurring peptide, consisting of the sequence of SEQ ID NO: 1 operably linked to a cell penetrating peptide.

2. The non-naturally occurring peptide of claim 1, wherein the cell penetrating peptide is selected from the group consisting of a HIV-TAT peptide, a penetratin peptide, a polyarginine peptide, a pep-1 peptide, and a transportin peptide.

3. The non-naturally occurring peptide of claim 2, wherein the cell-penetrating peptide is a HIV-TAT peptide.

4. The non-naturally occurring peptide of claim 3, wherein the non-naturally occurring peptide consists of the sequence of SEQ ID NO: 3.

5. A vector, consisting of a nucleic acid encoding a non-naturally occurring peptide having the sequence of SEQ ID NO: 1 operably linked to an expression cassette.

6. A composition, comprising a non-naturally occurring peptide and a pharmaceutically-acceptable vehicle, carrier, or excipient, the non-naturally occurring peptide consisting of the sequence of SEQ ID NO: 1 operably linked to a cell penetrating peptide.

7. The pharmaceutical composition of claim 6, further comprising an additional therapeutic agent.

8. The pharmaceutical composition of claim 7, wherein the additional therapeutic composition is selected from the group consisting of a chemotherapeutic agent, a toxin, an immunological response modifier, an enzyme, and a radioisotope.

9. The pharmaceutical composition of claim 6, wherein the non-naturally occurring peptide is included in the composition in an amount sufficient to affect a cellular process selected from the group consisting of: antagonizing a cardiotonic steroid (CTS) induced protein kinase cascade; upregulating a CTS induced protein kinase cascade; Src inhibition; Src stimulation; Na/K-ATPase mimic; Na/K-ATPase competitive inhibitor; Lyn inhibition; Lyn stimulation; ouabain antagonism; ouabain stimulation; ERK1/2 activation; ERK1/2 inhibition; membrane permeability by sodium ions; and membrane permeability by potassium ions.

10. The pharmaceutical composition of claim 6, wherein the non-naturally occurring peptide binds to Src with an IC50 of less than about 10 µM.

11. A method of treating a Src-associated disease, comprising administering an effective amount of a non-naturally occurring peptide consisting of the sequence of SEQ ID NO: 1 to a subject in need thereof.

12. The method of claim 11, wherein the Src-associated disease is selected from the group consisting of cancer, vascular disease, cardiovascular disease, tissue fibrosis, and osteoporosis.

13. The method of claim 12, wherein the Src-associated disease is cancer, and wherein the cancer is selected from the group consisting of prostate cancer, breast cancer, and neuroblastoma.

14. The method of claim 12, wherein the Src-associated disease is cardiovascular disease, and wherein the cardiovascular disease is selected from the group consisting of heart disease, cardiac hypertrophy, congestive heart failure, and ischemia-reperfusion injury.

15. The method of claim 12, wherein the non-naturally occurring peptide consists of the sequence of SEQ ID NO: 3.

16. A method for reducing Src activity in a cell, comprising contacting a cell with an effective amount of a peptide consisting of the sequence of SEQ ID NO: 1 operably linked to a cell penetrating peptide.

17. The method of claim 16, wherein the cell is selected from the group consisting of a monocyte, a heart cell, a liver cell, a vascular cell, a breast cell, a prostate cell, a kidney cell, a muscle cell, a brain cell, bone cell, and a tumor cell.

18. The method of claim 16, wherein the non-naturally occurring peptide consists of the sequence of SEQ ID NO: 3.

* * * * *

SEQUENCE LISTING

```
<160> NUMBER OF SEQ ID NOS: 10

<210> SEQ ID NO 1
<211> LENGTH: 18
<212> TYPE: PRT
<213> ORGANISM: Homo sapiens
<220> FEATURE:
<221> NAME/KEY: Phosphorylation
<222> LOCATION: (15)..(15)

<400> SEQUENCE: 1

Ser Thr Asn Cys Val Glu Gly Thr Ala Arg Gly Ile Val Val Tyr Thr
1               5                   10                  15

Gly Asp

<210> SEQ ID NO 2
<211> LENGTH: 18
<212> TYPE: PRT
<213> ORGANISM: Homo sapiens

<400> SEQUENCE: 2

Ser Thr Asn Cys Val Glu Gly Thr Ala Arg Gly Ile Val Val Tyr Thr
1               5                   10                  15

Gly Asp

<210> SEQ ID NO 3
<211> LENGTH: 31
<212> TYPE: PRT
<213> ORGANISM: Artificial Sequence
<220> FEATURE:
<223> OTHER INFORMATION: HIV-TAT - pNaSH2 Fusion Peptide
<220> FEATURE:
<221> NAME/KEY: Phosphorylation
<222> LOCATION: (28)..(28)

<400> SEQUENCE: 3

Gly Arg Lys Lys Arg Arg Gln Arg Arg Pro Pro Gln Ser Thr Asn
1               5                   10                  15

Cys Val Glu Gly Thr Ala Arg Gly Ile Val Val Tyr Thr Gly Asp
                20                  25                  30

<210> SEQ ID NO 4
<211> LENGTH: 31
<212> TYPE: PRT
<213> ORGANISM: Artificial Sequence
<220> FEATURE:
<223> OTHER INFORMATION: HIV-TAT NaSH2 Fusion Peptide

<400> SEQUENCE: 4
```

```
Gly Arg Lys Lys Arg Arg Gln Arg Arg Pro Pro Gln Ser Thr Asn
1               5                   10                  15

Cys Val Glu Gly Thr Ala Arg Gly Ile Val Val Tyr Thr Gly Asp
            20                  25                  30

<210> SEQ ID NO 5
<211> LENGTH: 10
<212> TYPE: PRT
<213> ORGANISM: Human immunodeficiency virus

<400> SEQUENCE: 5

Gly Arg Lys Lys Arg Arg Gln Arg Arg Arg
1               5                   10

<210> SEQ ID NO 6
<211> LENGTH: 16
<212> TYPE: PRT
<213> ORGANISM: Drosophila melanogaster

<400> SEQUENCE: 6

Ala Lys Ile Trp Phe Gln Asn Arg Arg Met Lys Trp Lys Lys Glu Asn
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Arg Arg Arg Arg Arg Arg Arg Arg Arg
1               5

<210> SEQ ID NO 8
<211> LENGTH: 21
<212> TYPE: PRT
<213> ORGANISM: Simian virus 40

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 136
<212> TYPE: PRT
<213> ORGANISM: Homo sapiens

<400> SEQUENCE: 10
```

-continued

```
Lys Ser Ser Lys Ile Met Glu Ser Phe Lys Asn Met Val Pro Gln Gln
1               5                   10                  15

Ala Leu Val Ile Arg Asn Gly Glu Lys Met Ser Ile Asn Ala Glu Glu
            20                  25                  30

Val Val Val Gly Asp Leu Val Glu Val Lys Gly Gly Asp Arg Ile Pro
        35                  40                  45

Ala Asp Leu Arg Ile Ile Ser Ala Asn Gly Cys Lys Val Asp Asn Ser
        50                  55                  60

Ser Leu Thr Gly Glu Ser Glu Pro Gln Thr Arg Ser Pro Asp Phe Thr
65                  70                  75                  80

Asn Glu Asn Pro Leu Glu Thr Arg Asn Ile Ala Phe Phe Ser Thr Asn
                85                  90                  95

Cys Val Glu Gly Thr Ala Arg Gly Ile Val Val Tyr Thr Gly Asp Arg
            100                 105                 110

Thr Val Met Gly Arg Ile Ala Thr Leu Ala Ser Gly Leu Glu Gly Gly
        115                 120                 125

Gln Thr Pro Ile Ala Ala Glu Ile
    130                 135
```